United States Patent [19]

Golias et al.

[11] Patent Number: 5,055,271

[45] Date of Patent: Oct. 8, 1991

[54] PUMP INSERTER FOR TEST TUBES

[75] Inventors: Tipton L. Golias; Ovay H. Mayes; Robert J. Sarrine, all of Beaumont, Tex.

[73] Assignee: Helena Laboratories Corporation, Beaumont, Tex.

[21] Appl. No.: 383,339

[22] Filed: Jul. 24, 1989

[51] Int. Cl.$^5$ .............................................. B01L 9/00
[52] U.S. Cl. .................................... 422/99; 422/100; 422/103; 422/63; 436/48; 73/864.17; 73/864.87; 73/863.31; 73/863.32
[58] Field of Search .................. 422/99, 100, 103, 63; 436/48; 73/864.17, 864.87, 863.31, 863.32

[56] References Cited

U.S. PATENT DOCUMENTS

| | | | |
|---|---|---|---|
| 3,687,175 | 8/1972 | Babey | 422/99 |
| 4,301,116 | 11/1981 | Ida et al. | 422/63 |
| 4,478,094 | 10/1984 | Salomaa et al. | 73/863.32 |
| 4,554,839 | 11/1985 | Hewett et al. | 73/863.32 |
| 4,605,536 | 8/1986 | Kuhnert et al. | 422/99 |
| 4,779,467 | 10/1988 | Rainin et al. | 73/864.17 |
| 4,812,293 | 3/1989 | McLaurin et al. | 422/102 |

OTHER PUBLICATIONS

Technical Brief, Zymark Corporation, copyright 1985.

Primary Examiner—David L. Lacey
Assistant Examiner—Abanti B. Singla
Attorney, Agent, or Firm—Spencer & Frank

[57] ABSTRACT

Apparatus for securing pump mechanisms to test tubes sealed by a closure such that the contents of the test tubes may be discharged without removing the closure. The apparatus includes a rack for holding a plurality of pump mechanisms, each of the pump mechanisms including a downwardly extending needle or the like for penetrating the closure of the test tube. The test tubes are arranged within a tray in a plurality of rows, and each row is sequentially advanced into position. As each row is in position, the pump mechanism is moved toward the row of test tubes to penetrate the test tube closures. The pump mechanisms thereafter released, the rack filled with a next series of pump mechanisms, the test tube array indexed, and the cycle of steps is repeated. The pump mechanism needles are initially imbedded in a protective packaging. The apparatus strips away the protective packaging to expose the sharpened points or tips of the pump mechanism.

8 Claims, 4 Drawing Sheets

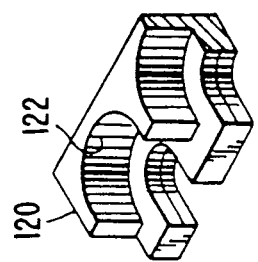
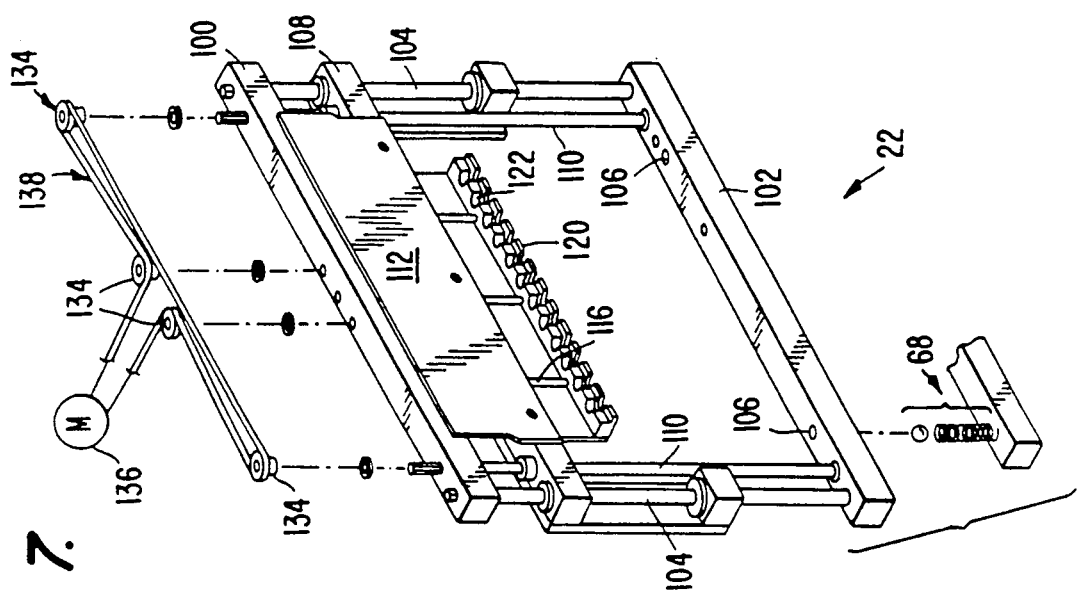
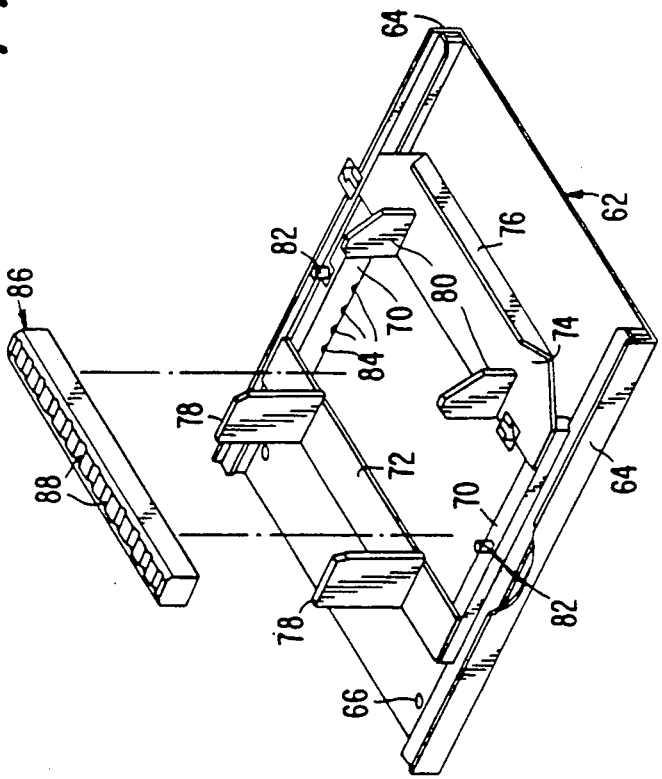

PUMP INSERTER FOR TEST TUBES

BACKGROUND OF THE INVENTION

The present invention relates to test tubes in general, and more particularly, to an apparatus for inserting pump mechanisms into test tubes which are sealed by a closure such that the contents of the test tube may be discharged without removing the closure from the test tube.

Heretofore it has been known to provide a resilient closure or rubber stopper for a container and to discharge the contents of the container by first establishing inlet and outlet flow paths through the closure. Air pressure through the inlet path pressurizes the interior of the container and causes the contents to flow through the outlet path. Devices of this type are, of course, known and, prior to the present invention, the establishing of the fluid flow paths was accomplished by manually puncturing the closure with a pump mechanism.

There are, of course, numerous concerns when puncturing the closure of a test tube. A fundamental problem, of course, is that a test tube is formed of glass and, therefore, is subjected to breaking if excessive forces are utilized. Equally important is the need to align the direction of force relative to the elongated axis of the test tube to provide proper positioning of the pump mechanism. Furthermore, the amount of force necessary to penetrate or puncture the test tube closure will be minimized if the direction of the inserting force is along the longitudinal axis of the test tube rather than at an angle to the longitudinal axis of the test tube. Yet another problem in connection with manually attaching pump mechanisms to test tubes by puncturing test tube closures is the difficulty in handling such mechanisms because of their relatively small size. A still further problem is the amount of time and labor involved in attaching pump mechanisms to a large quantity of test tubes if each pump must be attached manually and sequentially, on an individual basis, rather than attaching a plurality of pump mechanisms simultaneously to individual test tubes.

SUMMARY OF THE INVENTION

The present invention overcomes these shortcomings by providing an apparatus for inserting pump mechanisms, or parts of pump mechanisms, through test tube closures.

The present invention contemplates the simultaneous insertion of a plurality of pump mechanisms, or parts thereof, through the respective closures of a plurality of test tubes.

The present invention also contemplates protecting the individual test tubes from breakage and aligning the test tubes and the pump mechanisms relative to each other such that forces applied for insertion of the pump mechanisms through the test tube closures are aligned relative to the longitudinal axes of the test tubes, thereby minimizing the necessary force and reducing the rate of breakage and damage.

The present invention further contemplates an apparatus whereby a plurality of pump mechanisms are withdrawn from a holder and retained in a desired position relative to the test tubes and whereby an array of test tubes may be selectively indexed such that the pump mechanisms may be inserted through the closures of the desired test tubes.

BRIEF DESCRIPTION OF THE DRAWINGS

The foregoing benefits and advantages of the present invention will be more fully understood upon reading the following detailed description of the invention taken in conjunction with the drawings.

In the drawings, wherein like reference numerals identify corresponding components:

FIG. 6 is an enlarged, partially exploded perspective illustration of a tray slide according to the principles of the present invention;

FIG. 7 is a partially exploded front perspective illustration of an assembly for inserting the pump mechanisms into the test tubes;

FIG. 8 is a perspective illustration of a portion of the assembly of FIG. 7.

DETAILED DESCRIPTION OF THE INVENTION

Figure 1:
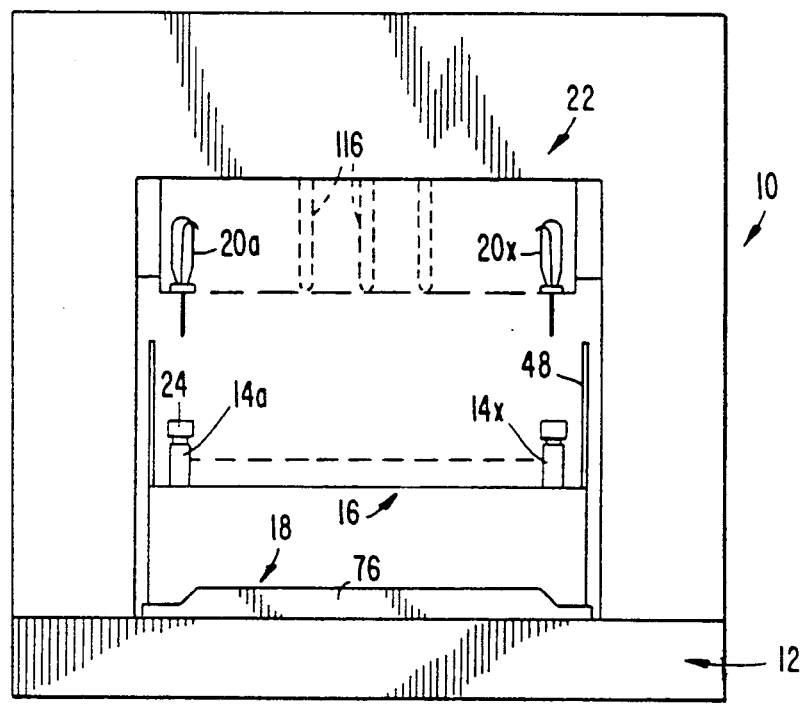
FIG. 1 is an elevation view of an apparatus according to the principles of the present invention with pump mechanisms illustrated at a first station and test tubes illustrated at a second station.

Referring to the drawings, FIG. 1 provides an overall front elevation illustration of the present invention including a housing 10 supported on a chassis 12. A plurality of test tubes 14a...14x are mounted in a test tube tray 16, and the tray is removably positioned on a slide 18. The slide 18 is mounted for sliding movement forwardly and rearwardly relative to the chassis 12. A plurality of pump mechanisms 20a...20x are mounted in a drive system 22 and are moved vertically downwardly to be attached to the test tubes.

Figure 3:
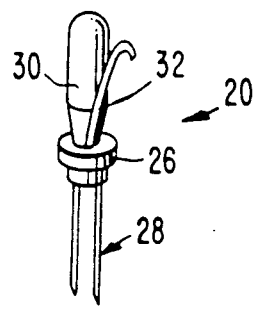
FIG. 3 is a perspective illustration of one form of a pump mechanism.

Specifically, the pump mechanisms are positioned at a first station and the slide 18 is indexable at a second station aligned vertically below the first station. A row of test tubes is positioned in tray 16 which is mounted in slide 18, and each test tube 14 is closed or sealed with a rubber closure or cap 24. Referring to FIG. 3, each pump mechanism 20 includes a generally circular disk 26, and extending downwardly from each disk are one or more hollow cannulas or needles 28 for providing inlet and outlet fluid flow paths. On the opposite side of the disk 26 from the needles 28, a compressible bulb or bellows 30 is provided as well as an outlet o delivery tube 32. The interior of the delivery tube 32 is in fluid communication with the interior of one of the needles 28 such that as the needles 28 are inserted through the closure 24 of a test tube and bellows 30 actuated, air is pressurized within the test tube causing the contents of the test tube to be discharged through the delivery tube 32.

Figure 5:
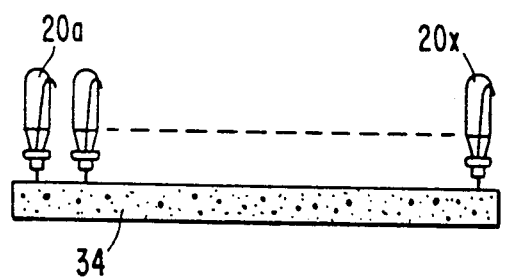
FIG. 5 is an elevation view of a plurality of pump mechanisms positioned in a holder.
Figure 9:
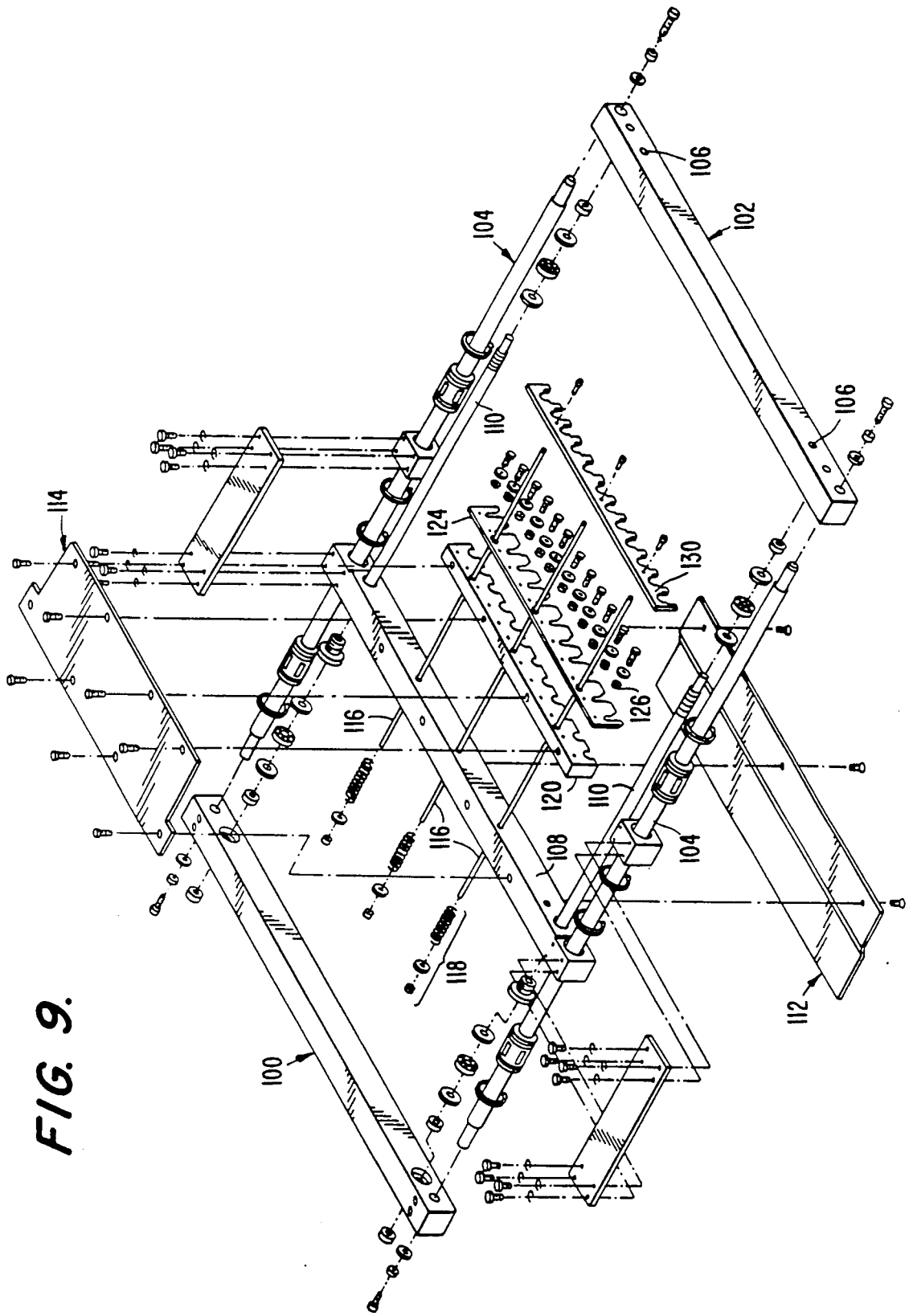
FIG. 9 is a exploded rear perspective partial illustration of the apparatus of FIG. 7.

As illustrated generally in FIG. 5, a plurality of pump mechanisms 20a...20x may be initially aligned in a straight line relative to protector such as a block 34 preferably made of styrofoam or the like, with the needles 28 being inserted into the block 34. Although not shown in FIG. 5, the underside of the disk 26 will function to limit the depth of insertion of each pump mechanism 20 into the styrofoam block 34. The collection of pumps mounted within a styrofoam block 34 is loaded into the pump drive system at the first station, and then the pump drive moves vertically to first strip the styrofoam block 34 from the pump needles and thereafter move the needles into engagement with the closures 24 on the respective test tubes such that the needles 28 puncture and are inserted into the test tubes. Thereafter, the pump mechanisms are disengaged from the pump drive, and the slide 18 may be moved to bring another row of test tubes into position under the first station. Then another block 34 loaded with pump mechanisms is loaded into the drive system 22, and the sequence of steps repeated to attach pump mechanisms to a second row of test tubes.

Figure 4:
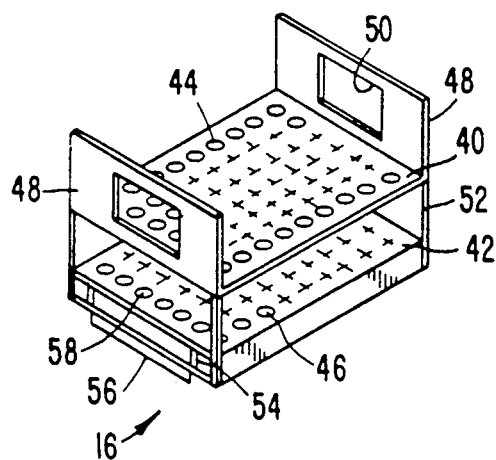
FIG. 4 is a perspective illustration of a rack for holding a plurality of test tubes.

Referring next to FIG. 4, the details of the tray 16 for supporting an array of test tubes will now be explained. The tray 16 is formed as a generally open framework including upper and lower generally horizontally positioned thin plates 40 and 42. Plate 40 has an array of apertures 44 therein, and plate 42 has an array of apertures 46 therein, apertures 44 and 46 being vertically aligned. At opposite ends of the upper plate 40 are a pair of end members 48, each of which contains a large aperture 50 such that the tray may be conveniently lifted and moved. Vertical supports 52 are provided to interconnect the upper and lower plates and maintain them rigidly secured together, and additional supports 54 are secured to the lower plate 42 and depend downwardly therefrom to maintain the plate 42 above a base 56. A base 56 is provided at each end of the tray, and supports 54 are of sufficient length such that when the base 56 rests on a horizontal surface and test tubes are inserted through the apertures in the respective plates, the bottoms of the test tubes will not contact the horizontal surface. Also provided in the lower plate 42 are alignment apertures 58 (only one is shown) to assist in aligning and indexing the tray as will hereinafter be described.

Figure 2:
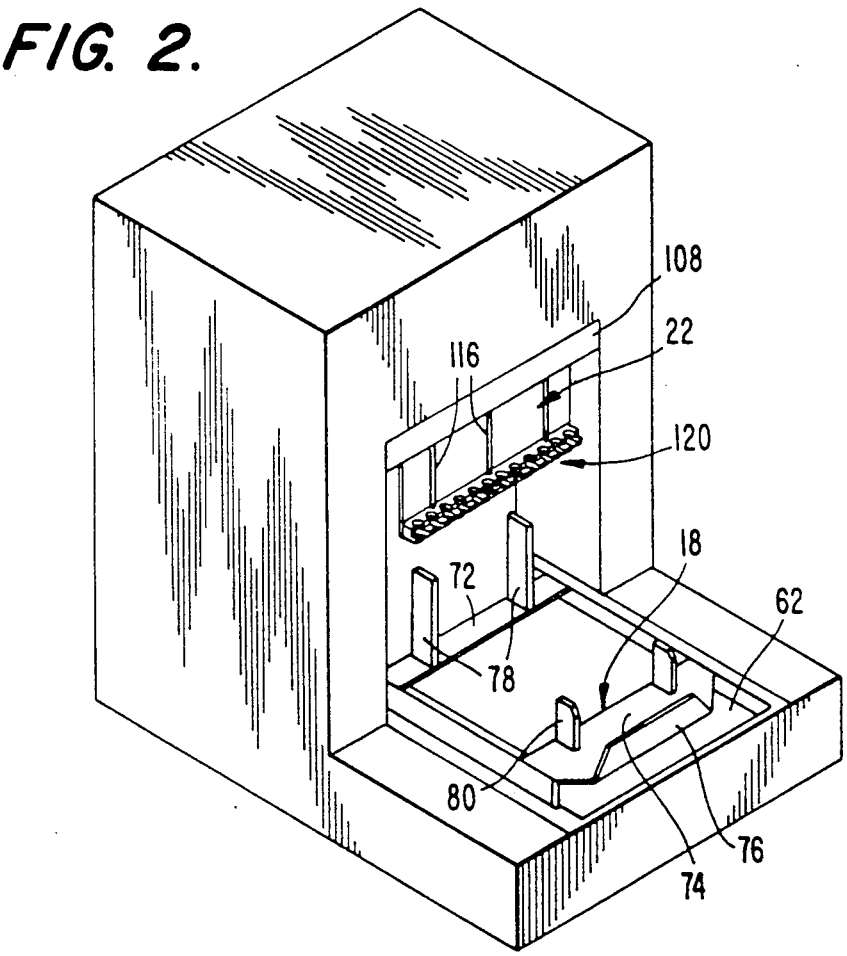
FIG. 2 is a perspective illustration of the apparatus of the present invention with the test tubes and pump mechanisms removed.

Referring next to FIGS. 1, 2 and 6, details of the slide 18 will now be provided. The slide 18 includes a floor 62 which is of generally rectangular configuration. A pair of elongated tracks 64 are secured to opposite sides of the floor, extending from the front to the rear. The floor 62 is secured to the chassis 12 and is provided with apertures 66 at opposite sides thereof which function in cooperation with detents 68 for indexing the position of the slide as will be explained in greater detail.

The slide 18 further includes a pair of elongated bars 70 extending generally parallel to the tracks 64, and each bar 70 is provided with a groove to engage its respective track 64. A first strap plate 72 extends laterally between the elongated bars and is secured to both of the bars at one end thereof, and a second strap plate 74 extends laterally between the elongated bars and is secured thereto at the other end of the bars, such that the two bars 70 and the two strap plates 72, 74 form a rectangular frame. The front plate 74 has an upwardly-turned flange or lip 76. A pair of blocks 78 extend vertically upwardly from the rear strap plate 72, and a pair of blocks 80 extend vertically upwardly from the front strap plate 74. These four blocks serve as guides such that the tray 16, with the test tubes therein, will be generally positioned between these four blocks. Thus, the rear blocks limit the rearward tray movement, and the front blocks limit forward tray movement. Each of the bars 70 includes an upwardly extending pin 82 to engage the apertures 58 in the lower plate 42 of the tray 16. In this fashion, there is positive alignment between the test tube tray 16 and the rectangular frame of the slide 18. The bars 70 each include a plurality of transverse notches 84 on their underside to engage the detent 68 as will be further explained.

Intermediate the front and rear strap plates, 74, 72 is a pressure block 86 which is secured to the floor 62. This pressure block 86 has a plurality of recesses 88 therein shaped to engage and support the bottoms of the test tubes during the time that the test tubes are subjected to pressure. Since floor 62 is secured to the chassis 12, the pressure block 86 is fixed relative to the second station such that as each succeeding row of test tubes is indexed to the second station, the row of test tubes for which pump mechanisms are being inserted will be positioned above the pressure block. The pressure block is made out of a resilient plastic such as Delrin, and the opposed bars 70 which slide along the frame 64 may also be made of Delrin plastic.

Referring next to FIGS. 2, 7, 8 and 9, the pump drive assembly 22 will now be explained in greater detail. It should be understood and appreciated that the apparatus is symmetrical relative to a vertical plane and thus, as viewed from the front elevation view, the left side of the apparatus is the mirror image of the right side. The pump drive assembly includes a generally rectangular vertically positioned framework. It should be pointed out that in FIG. 7 the pump drive assembly 22 is seen from the front of the apparatus, while in FIG. 9 the pump drive assembly is viewed from the rear of the apparatus. The generally rectangular framework for the pump drive apparatus includes a top generally rectangular bar 100 and a bottom generally rectangular bar 102 interconnected by two bearing shafts 104. The bearing shafts 104 are positioned at opposite ends of the bars 100, 102 to provide a generally rectangular framework. The bottom bar 102 is secured to the chassis and is provided with apertures 106 to receive the detent means 68. Detent means 68 is illustrated as a spring loaded bearing (only one is illustrated) such that the bearing will extend through apertures 66 in slide 18 to sequentially engage notches 84 as the slide carrying the tray 16 is moved inwardly and outwardly of the housing. Thus, the tray, and slide, are indexable relative to the bottom bar 102.

Means are provided for retaining the series of pump mechanisms 20 and for inserting the needles of the pump mechanisms through the closures of the test tubes. Specifically, a rectangular bar 108 is horizontally positioned parallel to, and intermediate, bars 100, 102. Bar 108 is provided with apertures at either end, extending vertically therethrough, the apertures being fitted with bushings, as is conventional, such that the bar 108 can move vertically on the bearing shafts 104. A pair of power screws or long, threaded shafts 110 are provided and vertically aligned at opposite ends of the frame assembly laterally inwardly of the bearing shafts 104. Each of the threaded power screws 110 has one end mounted through conventional thrust bearings into the bottom bar 102 such that the power screws may rotate freely relative to the bottom bar 102. Each power screw 110 is also provided at its top end with bearings and extends through suitable apertures in the top bar 100 for free rotation within the bar. The tops of the bearing screws 110 extending upwardly through the top bar 100, and through conventional bearings and bushings, are connected to a drive mechanism which causes rotation of the two power screws. Each of the power screws extends through threaded apertures within the middle bar 108 such that rotation of the power screws causes movement either upwardly or downwardly of the middle bar 108. This explains, in general terms, the framework and movement of the pump drive mechanism 22.

Continuing to refer to these Figures, a plate 112 is secured to the front of the bar 108, and a second plate 114 is secured to the rear of the bar 108. The bar 108 has a plurality of push rods 116 extending vertically therethrough, suitable apertures being thus provided in the bar 108, and compression springs, clips and washers collectively identified as 118 are provided surrounding the push rods 116 and positioned above the middle bar 108. On the opposite side of the bar 108 from the compression springs, a pressure bar 120 is provided. The pressure bar 120 is also secured to the pressure plate 114 and thus the distance between the pressure bar 120 and the middle bar 108 is fixed. The pressure bar 120 has a plurality of recesses 122 therein to receive the bellows or compressible bulb of the pump mechanisms. Mounted on the push rods 116 and positioned slightly below the pressure bar 120 is a spring plate member 124. The push rods extend through suitably apertures in the spring plate 124 and the spring plate 124 is secured to the pressure bar 120 by a plurality of screws. Resilient O-rings 126 are provided on the side of the spring plate 124 opposite from the pressure bar 120 such that the spring plate may be moved a slight distance away from the pressure bar 120 thereby compressing the O-rings. This feature allows the disks 26 of the pump assemblies to be forced between the pressure bar 120 and the spring plate 124. The spring plate 124 is a thin, flat, metal spring which also has a series of recesses therein to accommodate the downwardly depending needles 28 of the pump mechanisms. Positioned at the opposite end of the push rods 116 from the compression springs is an ejector plate 130 which is also generally configured similar to pressure bar 120 and spring plate 124 in that there are a row or series of semicircular recesses to receive the needles 28 of the pump mechanisms.

The operation of the pump drive will now be explained. Consider the situation where a plurality of pump mechanisms having their needles embedding in a block 34 of styrofoam with the pump mechanisms aligned along the block. The tray 16 containing an array of test tubes is placed within the slide 18 and moved to a first detent position such that the first row of test tubes are positioned in a first station under the middle bar 108 of the pump drive assembly 22. The operator of the equipment moves the block 34 of styrofoam into position such that the disks 26 on each of the pump assemblies are captured between the pressure bar 120 and the spring plate 124. The drive mechanism causes the middle bar 108 initially to move upwardly. As the middle bar 108 moves upwardly, the push rods 116 engage the underside of the top bar 100, thus preventing any further movement of the ejector plate 130. As the bar 108 continues to move upwardly, the ejector plate contacts the top of the styrofoam block and strips the styrofoam block from the needles.

Continuing with the operation of the drive mechanism, the middle bar 108 begins to move downwardly toward the row of test tubes. Force from the middle bar 108 is transferred in part through the pressure plate 114 to the pressure bar 120 and thus the downward force causes the needles to be inserted through the closures of the test tubes. Thereafter, the middle bar 108 is moved upwardly and stops at a rest position previously called the first station. Then the cycle may be repeated commencing with movement of the slide 18 inwardly to align a second row of test tubes under the pump drive, taking yet another block 34 with needles of pump mechanisms embedded therein and loading the pump mechanisms between the pressure bar 120 and the spring plate 124 stripping the protective block from the needles and thereafter inserting the needles into the sealed test tubes.

Referring back to FIG. 7, a drive mechanism is diagrammatically shown attached to the upper ends of the threaded power screws 110. The drive mechanism is diagrammatically shown as a series of drive sprockets 134 connected to a motor 136 via a drive belt or chain 138.

The entire system is preferably operated under microprocessor control as is conventional for the operation of a reversible motor where movement through short distances in a multi-part cycle of operation is desired.

Thus, it may be appreciated that the present invention attaches pump mechanisms to sealed test tubes by holding the pump mechanisms at a first station, supporting the test tubes at a second station which is aligned under the first station, moving the pump mechanisms away from the first station to remove any protective covering on the pump mechanisms, and thereafter moving the pump mechanisms toward said second station to cause the pump mechanisms to be attached to the test tubes. In the preferred embodiment, the pump mechanisms have sharpened needles or cannulas which puncture the closures which seal the test tubes.

The foregoing is a complete description of a preferred embodiment of the present invention. Numerous changes, modifications and improvements may be made without departing from the spirit and scope of the present invention. The present invention, therefore, should be limited only by the following claims.

What is claimed is:

1. Apparatus for attaching pump mechanisms to sealed test tubes, each test tube sealed by a resilient, puncturable closure, comprising:
   means for releasably supporting a plurality of pump mechanisms;
   a support frame;
   means for holding the plurality of pump mechanisms while supported by said supporting means at a first station, said holding means secured to said support frame;
   removing means connected with said frame for removing said supporting means from the plurality of pump mechanisms;
   means for positioning a plurality of test tubes at a second station, said positioning means engaging said support frame; and
   means for moving said holding means from said first station toward said second station after removal of said supporting means, which causes said moving means to move plurality of pump mechanisms to a position for attachment to respective ones of the test tubes.

2. The apparatus as defined in claim 1, wherein said moving means further comprising puncturing means, constructed so as to cause puncturing of
   the closure of a respective one of the test tubes at said second station.

3. The apparatus as defined in claim 1 wherein said test tube positioning means includes means for sequentially positioning a plurality of rows of test tubes at said second station.

4. The apparatus as defined in claim 2, wherein
said supporting means includes a protector for each of the plurality of pump mechanisms; and
said removing means is constructed so as to remove simultaneously the protector from each of the puncturing means.

5. The apparatus as defined in claim 4,
each pump mechanism of the plurality of pump mechanisms includes a portion removed from the puncturing means;
said holding means includes means for grasping the portions; and
said removing means is constructed so as to move away from said grasping means for removing said protector.

6. The combination as defined in claim 5, wherein
said removing means is constructed so as to move in a direction away from said holding means for removing said protector.

7. The combination as defined in claim 5, wherein
said grasping means comprises a pressure bar in communication with a spring plate each having aligned spaced recesses, and means for biasing said pressure bar and said spring plate toward one another for grasping therebetween said portions of the pump mechanisms in the aligned recesses.

8. The invention as defined in claim 7, wherein
said removing means comprises an ejector plate which is mounted so as to move relative to said grasping means and said removing means having spaced recesses aligned with the recesses of said pressure bar and said spring plate.

* * * * *